United States Patent [19]

Yamabe et al.

[11] 4,379,768
[45] Apr. 12, 1983

[54] PROCESS FOR PRODUCING PERFLUOROSUCCINYL FLUORIDE

[75] Inventors: Masaaki Yamabe, Machida; Seiji Munekata; Seisaku Kumai, both of Tokyo; Isamu Kaneko, Yamato, all of Japan

[73] Assignee: Asahi Glass Company, Ltd., Yamato, Japan

[21] Appl. No.: 296,363

[22] Filed: Aug. 26, 1981

[30] Foreign Application Priority Data

Aug. 26, 1980 [JP] Japan .................................. 55-116401

[51] Int. Cl.³ ............................................ C07C 51/58
[52] U.S. Cl. ................................................ 260/544 F
[58] Field of Search ..................................... 260/544 F

[56] References Cited
FOREIGN PATENT DOCUMENTS 2052501 1/1981 United Kingdom ............ 260/544 F

OTHER PUBLICATIONS

Migrdichian, Vartkes, "Organic Synthesis", (1957), p. 1225, Reinhold, Publ.
Tsonkalas, Skevos N., *Chemical Abstracts,* vol. 66, (1967), #85,384p.

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

Perfluorosuccinyl fluoride is produced by coupling accompanied by dehalogenation of a difluorohaloacetyl fluoride having the formula $$XCF_2COF$$

wherein X represents I, Br or Cl by reacting with a trapping agent of a halogen at a temperature ranging from 100° to 500° C.

4 Claims, No Drawings

PROCESS FOR PRODUCING PERFLUOROSUCCINYL FLUORIDE

BACKGROUND OF THE INVENTION

1. Field of the Invention

The present invention relates to a process for producing perfluorosuccinyl fluoride which is useful as an intermediate for various fluorine-containing compounds or a compound having special characteristics. For example, perfluorosuccinyl fluoride can be converted into perfluorodicarboxylic acid derivatives useful as starting material for fluorine-containing condensation polymers having excellent thermal resistance and chemical stability such as polyamides and polyesters by reacting with a nucleophilic reagent. The perfluorocarbon ether acid fluorides derived from the succinyl fluoride by the addition of hexafluoropropylene oxide or tetrafluoroethylene oxide can be converted into perfluorocarbon ethers useful as lubricants, solvents and insulating materials having excellent thermal resistance chemical stability and insulating properties. The succinyl fluoride can be also used as a starting material for perfluorocarbon vinyl ethers useful as a source of polymers.

2. Description of the Prior Art

Heretofore, it has been known to produce perfluorosuccinyl fluoride by the following processes:
(1) An electro chemical fluorination of succinyl fluoride
(2) An oxidation of perfluorocyclobutene
(3) An oxidation of 1,4-diiodoperfluorobutane
In these known processes, the yield of perfluorosuccinyl fluoride as the object product is low and the processes are not satisfactory for an industrial operation.

SUMMARY OF THE INVENTION

It is an object of the present invention to provide a process for producing perfluorosuccinyl fluoride having high purity at a high yield in a simple operation.

The foregoing and other objects of the present invention have been attained by a process for producing perfluorosuccinyl fluoride which comprises coupling accompanied by dehalogenation of a difluorohaloacetyl fluoride having the formula $XCF_2COF$ 

wherein X represents, I, Br or Cl by reacting with a trapping agent of a halogen at a temperature ranging from 100° to 500° C.

DETAILED DESCRIPTION OF THE PREFERRED EMBODIMENTS

As a result of various studies to overcome the aforementioned problems, it has been found that perfluorosuccinyl fluoride can be produced at a high yield by coupling accompanied by dehalogenation of a difluorohaloacetyl fluoride as a starting material under a specific condition.

In the process of the present invention, the difluorohaloacetyl fluoride as the starting material is important. The perfluorosuccinyl fluoride can be produced at a high yield by an one step reaction using a difluoroacetyl fluoride. On the other hand, it is difficult to attain a high yield by the known processes. The difluorohaloacetyl fluoride ($XCF_2COF$) used as the starting material in the present invention can be produced by various process depending upon the kind of X. For example, difluoroiodoacetyl fluoride (X=I) can be produced by a process in which lithium iodide is reacted with tetrafluoroethylene oxide or by a process which comprises decomposing the intermediate obtained by reacting sulfur trioxide with 1,2-diiodotetrafluoroethane. Difluorobromoacetyl fluoride (X=Br) can be produced by brominating difluoroiodoacetyl fluoride; by reacting oleum with 1,2-dibromotetrafluoroethane; or by decomposing the intermediate produced by reacting sulfur trioxide with 1,2-dibromochlorotrifluoroethane. Difluorochloroacetyl fluoride (X=Cl) can be obtained by similar processes.

The coupling accompanied by dehalogenation in the process of the present invention is preferably carried out under substantially anhydrous condition. Under the anhydrous condition, the coupling accompanied by dehalogenation is attained while maintaining the —COF group of difluorohaloacetyl fluoride active. When a moisture is present in the reaction, the difluorohaloacetyl fluoride as the starting material is hydrolyzed, whereby the formation of the difluorohaloacetic acid or sometimes oxalic acid results as a side reaction and the yield of perfluorosuccinyl fluoride is significantly reduced.

In the process of the present invention, it is important to perform the coupling accompanied by dehalogenation in the presence of a trapping agent of a halogen. When the reaction is carried out simply by heating without using a trapping agent of a halogen, it is necessary to heat to a considerably high temperature in obtaining a high conversion, and the yield of the object product is disadvantageously reduced by decomposition reactions.

The trapping agent of a halogen can be a metal such as copper and silver, and a metal couple such as zinc-copper. In view of easy handling, copper is used most preferably. The amount of the trapping agent of a halogen is determined depending upon the kind of the trapping agent and the kind of the difluorohaloacetyl fluoride used in the reaction. When a metal is used as the trapping agent of a halogen, the amount is usually in a range of 0.1 to 10 g. atom, preferably 0.5 to 8 g. atom to a mole of the difluorohaloacetyl fluoride, especially in the range of at least 4 g. atom based on difluoroiodoacetyl fluoride or at least 2 g. atom based on difluorobromoacetyl fluoride.

It is important to carry out the coupling accompanied by dehalogenation at a temperature ranging from 100° to 500° C. in the present invention. When the temperature is too low, the production of perfluoro(3-oxa-4-pentenoyl fluoride) as a by-product is predominant. On the other hand, when the temperature is too high, the decomposition becomes significant. In both cases, the yield of the object product is disadvantageously low. On the other hand, the reaction pressure is not critical and can be either reduced pressure or in a range of 0 to 100 kg/cm² gauge.

The reaction system for the coupling accompanied by dehalogenation in the present invention can either be a batch-wise reaction in which the difluorohaloacetyl fluoride and the trapping agent of a halogen are fed at the same time, or a continuous reaction in which the gaseous difluorohaloacetyl fluoride is passed through a bed packed with the trapping agent of a halogen. It is preferable to employ the continuous reaction in considering the efficiency of the reaction.

When the continuous reaction system is employed, it is preferable to use a fluidized bed as the packed bed in view of a smooth heat elimination and the reduction of the by product perfluorosuccinic acid anhydride. In this system, it is possible to attain the fluidization state with only the flow of the difluorohaloacetyl fluoride. It is preferable to feed a diluent gas in view of a smooth reaction. The diluent gas can be a gas inert to the difluorohaloacetyl fluoride, the trapping agent of a halogen and perfluorosuccinyl fluoride, for example, an inert gas such as nitrogen, helium and argon. The amount of the diluent gas is preferably selected from the range of 0.5 to 100 mole especially 1 to 20 mole per 1 mole of the difluorohaloacetyl fluoride.

In accordance with the process of the present invention, perfluorosuccinyl fluoride useful as an intermediate for various fluorine-containingcompounds can be obtained at a high yield in a simple process which consist of a coupling accompanied by dehalogenation of the difluorohaloacetyl fluoride. This is remarkably advantageous for an industrial operation.

The present invention will be further illustrated by certain examples and references which are provided for purposes of illustration only and are not intended to be limiting the present invention.

EXAMPLE 1

Into a 50 cc ampoule made of stainless steel equipped with a pressure gauge, 7.6 g. (0.12 g. atom) of metallic copper powder obtained by treating cupric sulfate with metallic zinc and drying at 200° C. under vacuum for 10 hours and 6.6 g. (0.029 mol) of difluoroiodoacetyl fluoride were charged. The atmosphere was substituted with nitrogen and then, the ampoule was heated by dipping in an oil bath maintained at 150° C. The inner pressure gradually rose to reach a maximum pressure of 12.8 kg./cm$^2$ gauge after about 10 minutes by the external heating and the exothermic heat resulting from the reaction. The inner pressure gradually decreased to 10.0 kg./cm$^2$ gauge after 65 minutes. The ampoule was taken out of the oil bath and cooled to room temperature (22° C.). The pressure was 3.0 kg./cm$^2$ gauge. Then, the reaction mixture was distilled under reduced pressure to recover the volatile matter. Gas chromatography and $^{19}$F-NMR spectroscopy showed that the volatile matter contained 1.9 g. of perfluorosuccinyl fluoride, 0.7 g. of perfluoro(3-oxa-4-pentenoyl fluoride) and 0.6 g. of the unreacted difluoroiodoacetyl fluoride.

EXAMPLE 2

Into a 50 cc ampoule made of stainless steel equipped with a pressure gauge, 12.7 g. of copper powder (100–200 mesh) and 18.2 g. of difluorobromoacetyl fluoride (BrCF$_2$COF) were charged and the ampoule was cooled to $-196°$ C. and degasified. Then, the ampoule was dipped into an oil bath maintained at 200° C. and heated for 8 hours. After the heating, 10.2 g. of organic compounds were recovered under reduced pressure from the ampoule. $^{19}$F-NMR spectroscopy showed that the recovered material contained 1.87 g. of the unreacted BrCF$_2$COF, 7.41 g. of perfluorosuccinyl fluoride, 0.50 g. of perfluoro(3-oxa-4-pentenoyl fluoride) and 0.42 g. of the other products.

EXAMPLE 3

Into a quartz tube having an inner diameter of 2.2 cm and a length of 50 cm which can be heated externally by an electric furnace, 63.6 g. of copper powder (100–200 mesh) was packed. The reaction tube was heated while passing nitrogen and the copper packed bed was maintained at 250° C. The gas fed into the copper packed bed was changed to BrCF$_2$COF, and the flow rate to 10.9 cc/min. During the operation, the outlet gas from the reaction tube was collected in a trap cooled to $-78°$ C. to give 8.96 g. of organic compounds. $^{19}$F-NMR spectroscopy showed that the product collected in the trap contained 0.17 g. of the unreacted BrCF$_2$COF, 6.06 g. of perfluorosuccinyl fluoride, 0.97 g. of perfluoro(3-oxa-4-pentenoyl fluoride) and 1.37 g. of perfluorosuccinic acid anhydride.

EXAMPLE 4

Into a reaction tube made of stainless steel having an inner diameter of 2.3 cm and a length of 70 cm fitted with a sintered metal porous plate and an external heater, 63.6 g. of copper powder (100 to 200 mesh) was packed and heated at 310° C. while passing nitrogen gas. Then, the gas for fluidizing the copper powder was changed from nitrogen to a mixture of nitrogen (150 N cc/min) and BrCF$_2$COF (14 N cc/min) for 3 hours. During the operation, the outlet gas from the reaction tube was condensed and collected in a trap cooled to $-78°$ C. The total amount of BrCF$_2$COF fed was 20.2 g. and the amount of the product collected in the trap was 11.3 g. $^{19}$F-NMR spectroscopy showed that the product contained 0.55 g. of the unreacted BrCF$_2$COF, 9.35 g. of perfluorosuccinyl fluoride, and 1.41 g. of perfluoro(3-oxa-pentenoyl fluoride).

EXAMPLE 5

The reaction was carried out as in Example 4 except decreasing the reaction temperature to 270° C. and changing the gas fed to a mixture of nitrogen (160 N cc/min) and ICF$_2$COF (15 N cc/min). The total amount of ICF$_2$COF fed was 2.7 g. and the amount of the condensed organic compounds was 11.9 g. $^{19}$F-NMR spectroscopy showed that the condensed product contained 0.82 g. of the unreacted ICF$_2$COF and 10.2 g. of perfluorosuccinyl fluoride.

We Claim:

1. A process for producing perfluorosuccinyl fluoride which comprises coupling accompanied by dehalogenation of a difluorohaloacetyl fluoride having the formula

XCF$_2$COF wherein X represents I, Br or Cl by reacting with a trapping agent of a halogen at a temperature ranging from 100° to 500° C.

2. The process according to claim 1 wherein said trapping agent of a halogen is copper.

3. The process according to claim 1 wherein said coupling accompanied by dehalogenation is carried out in a fluidized bed in which said trapping agent of a halogen is packed.

4. The process according to claim 3 wherein said coupling accompanied with dehalogenation is carried out in the presence of a gas inert to difluorohaloacetyl fluoride, a trapping agent of a halogen and perfluorosuccinyl fluoride.

* * * * *